United States Patent
O.K. Rahmat et al.

(10) Patent No.: US 9,498,141 B2
(45) Date of Patent: Nov. 22, 2016

(54) METHOD FOR DETERMINING RIGHT VENTRICLE STROKE VOLUME

(71) Applicant: Universiti Putra Malaysia, Serdang (MY)

(72) Inventors: Rahmita Wirza O.K. Rahmat, Serdang (MY); Anas A. Abboud, Serdang (MY); Mohd Zamrin Dimon, Serdang (MY); Suhaini Kadiman, Serdang (MY); M. Iqbal Saripan, Serdang (MY); Lili Nurliyana Abdullah, Serdang (MY)

(73) Assignee: Universiti Putra Malaysia, Serdang, Selangor (MY)

( * ) Notice: Subject to any disclaimer, the term of this patent is extended or adjusted under 35 U.S.C. 154(b) by 129 days.

(21) Appl. No.: 14/386,831

(22) PCT Filed: Mar. 22, 2013

(86) PCT No.: PCT/MY2013/000060
§ 371 (c)(1),
(2) Date: Sep. 22, 2014

(87) PCT Pub. No.: WO2013/141694
PCT Pub. Date: Sep. 26, 2013

(65) Prior Publication Data
US 2015/0078638 A1 Mar. 19, 2015

(30) Foreign Application Priority Data

Mar. 23, 2012 (MY) .......................... PI 2012001329

(51) Int. Cl.
*G06K 9/00* (2006.01)
*A61B 5/029* (2006.01)
(Continued)

(52) U.S. Cl.
CPC ............... *A61B 5/029* (2013.01); *A61B 8/065* (2013.01); *A61B 8/0883* (2013.01); *A61B 8/483* (2013.01);
(Continued)

(58) Field of Classification Search
None
See application file for complete search history.

(56) References Cited

U.S. PATENT DOCUMENTS

| | | | |
|---|---|---|---|
| 6,628,743 B1 | 9/2003 | Drummond et al. | |
| 2002/0123688 A1* | 9/2002 | Yamauchi | A61B 8/065 600/443 |

(Continued)

OTHER PUBLICATIONS

Shiota, Takahiro, et al. "Real-time three-dimensional echocardiography for determining right ventricular stroke volume in an animal model of chronic right ventricular volume overload." Circulation 97.19 (1998): 1897-1900.*

(Continued)

*Primary Examiner* — Stephen R Koziol
*Assistant Examiner* — Sean Conner
(74) *Attorney, Agent, or Firm* — Suzannah K. Sundby, Esq.; Canady + Lortz LLP

(57) ABSTRACT

The present invention relates to a method for determining right ventricle stroke volume comprising the steps of: providing a plurality of three-dimensional images of right cardiac ventricle of a patient over a cardiac cycle; identically slicing each of the plurality of images; selecting an image from the plurality of images, for each time unit of the cardiac cycle; determining a region of interest in each slice of the selected images, wherein the region of interest shows the right ventricle of the patient; determining area of the region of interest; determining volume of the region of interest; determining total volume of the region of interest for each time unit, wherein the maximum total volume is end diastolic volume and the minimum total volume is end systolic volume; and determining the right ventricle stroke volume using an equation:

Right Ventricle Stroke Volume=end diastolic volume−end systolic volume    (3).

4 Claims, 5 Drawing Sheets

(51) Int. Cl.
*A61B 8/06* (2006.01)
*A61B 8/08* (2006.01)
*G06T 7/00* (2006.01)
*G06T 7/60* (2006.01)

(52) U.S. Cl.
CPC ............. *A61B 8/523* (2013.01); *A61B 8/5223* (2013.01); *G06T 7/0083* (2013.01); *G06T 7/602* (2013.01); *G06T 2207/10132* (2013.01); *G06T 2207/10136* (2013.01); *G06T 2207/30048* (2013.01)

(56) References Cited

U.S. PATENT DOCUMENTS

| | | |
|---|---|---|
| 2004/0249297 A1 | 12/2004 | Pfeiffer et al. |
| 2005/0113665 A1 | 5/2005 | Mohr et al. |
| 2008/0249414 A1* | 10/2008 | Yang .................... A61B 8/0883 600/445 |
| 2008/0294057 A1 | 11/2008 | Parlikar et al. |
| 2011/0105931 A1 | 5/2011 | Qu et al. |
| 2011/0190634 A1* | 8/2011 | Kawagishi ............... A61B 8/14 600/443 |
| 2011/0301462 A1* | 12/2011 | Hashimoto .......... A61B 8/0883 600/443 |
| 2012/0078097 A1* | 3/2012 | Wang .................... G06T 7/2046 600/437 |
| 2014/0301624 A1* | 10/2014 | Barckow ............... G06T 7/0081 382/131 |

OTHER PUBLICATIONS

International Search Report received in PCT/MY2013/000060, mailed Jul. 10, 2013.

\* cited by examiner

METHOD FOR DETERMINING RIGHT VENTRICLE STROKE VOLUME

BACKGROUND OF THE INVENTION

Field of the Invention

This invention relates to a method for measuring stroke volume, and more particularly to a method for measuring stroke volume of a right ventricle.

Description of Related Arts

As early as 1950s-1970s, cardiologist recognised the importance of right ventricle function in heart filter, congenital heart disease and pulmonary hypertension. The assessment of right ventricle congenital function and anatomy remains a big challenge using two-dimensional echo because of its complex geometry. With poor resolution of two-dimensional image and the pre-processing which leads to possible loss of information, the right ventricle modelling is very difficult and inaccurate. The right ventricle stroke volume is an important measure of right ventricle function. Therefore, there is a need for an accurate method of measuring the stroke volume.

U.S. Pat. No. 4,674,518 disclosed a cardiac monitoring apparatus, more particularly to a method and apparatus for quantitatively measuring the instantaneous ventricular volume contained within a given chamber of a heart using an intracavity electrical impedance catheter having plural pairs of spaced surface electrodes driven by a corresponding plurality of electrical signals, each of the signals exhibiting a different discrete frequency, and having plural pairs of spaced surface electrodes for sensing the potentials at predetermined locations within the ventricle. The apparatus enable stroke volume and cardiac output to be continuously monitored. The cited patent involves the use of catheter which needs to be inserted into patient's body and this could cause discomfort and pain to the patient while the monitoring is taking place.

Kovalova et. Al. (2005) disclosed optimal geometric model for two-dimensional volumetry of right ventricle and its clinical validation. It disclosed that an ellipsoidal shell model best reflects the complex right ventricular geometry. Measurements of right ventricular stroke volume were made in modified apical four chamber and parasternal short axis views both in end-diastole and end-systole. The cited article mentioned that some of the result has poor quality of echocardiographic images. Besides that, the cited article used two-dimensional echocardiography which produces low precision of result and did not account for the variability of right ventricular outflow tract in patients.

Accordingly, it can be seen in the prior arts that there exists a need to provide a method for measuring stroke volume of right ventricle that is not painful to patient and has a better visualisation and accuracy of the end result.

REFERENCE

Kovalova, S., Necas, J., Cerbak, R., Malik, P., and Vespalec, J. (2005) "Echocardiographic Volumetry of The Right Ventricle", *European Journal of Echocardiography*, Vol. 6, page 15-23.

SUMMARY OF THE INVENTION

It is an objective of the present invention to provide a method for measuring stroke volume of right ventricle that is accurate and has involves minimal manual manipulation and correction.

It is also an objective of the present invention to provide a method for measuring stroke volume of right ventricle that provides good visualisation of the heart.

Accordingly, these objectives may be achieved by following the teachings of the present invention. The present invention relates to a method for determining right ventricle stroke volume comprising the steps of: providing a plurality of three-dimensional images of right cardiac ventricle of a patient over a cardiac cycle; identically slicing each of the plurality of images; selecting an image from the plurality of images, for each time unit of the cardiac cycle; determining a region of interest in each slice of the selected images, wherein the region of interest shows the right ventricle of the patient; determining area of the region of interest; determining volume of the region of interest; determining total volume of the region of interest for each time unit, wherein the maximum total volume is end diastolic volume and the minimum total volume is end systolic volume; and determining the right ventricle stroke volume using an equation:

$$\text{Right Ventricle Stroke Volume} = \text{end diastolic volume} - \text{end systolic volume} \quad (3)$$

BRIEF DESCRIPTION OF THE DRAWINGS

The features of the invention will be more readily understood and appreciated from the following detailed description when read in conjunction with the accompanying drawings of the preferred embodiment of the present invention, in which.

DETAILED DESCRIPTION OF THE INVENTION

Figure 1:
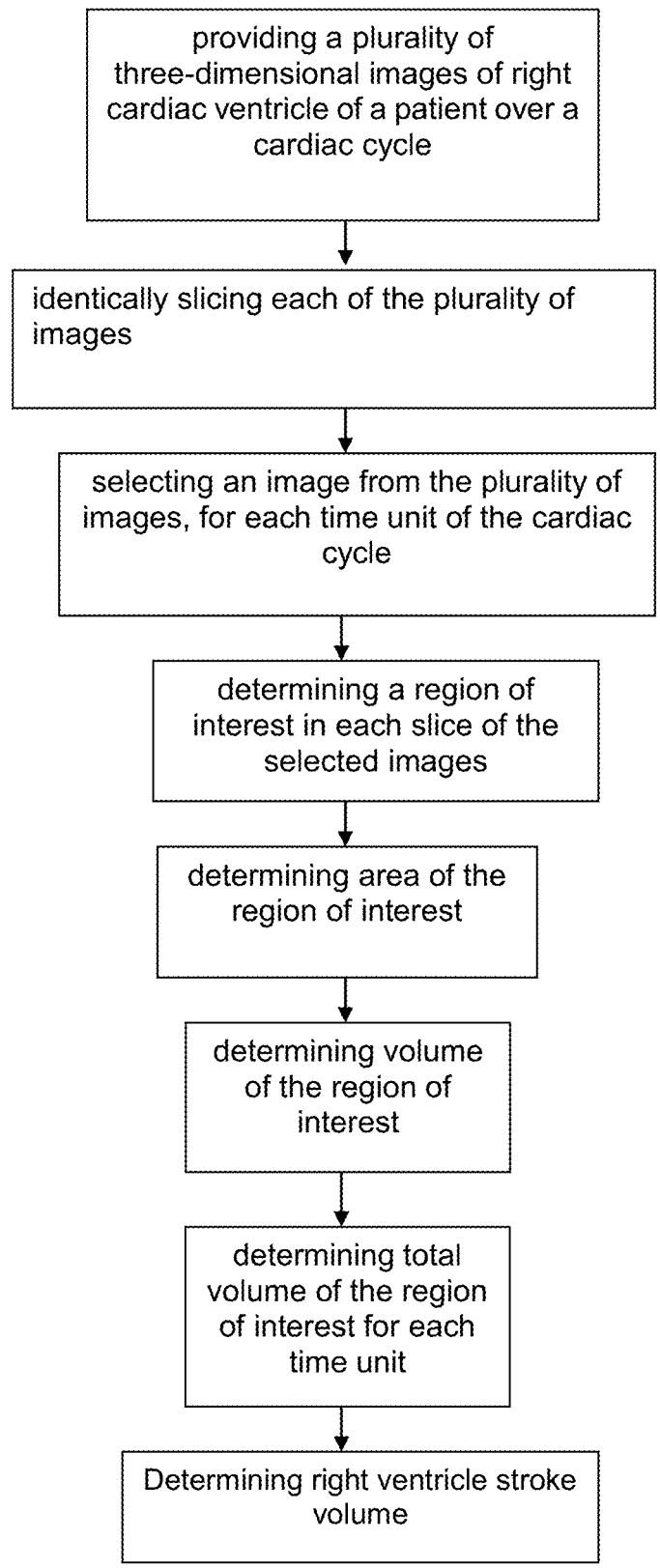
FIG. 1 is a flow chart of a method of measuring right ventricle stroke volume.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all modification, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations or technical terms are used, these indicate the commonly accepted meanings as known in the technical field. For ease of reference, common reference numerals will be used throughout the figures when referring to the same or similar features common to the figures. The present invention will now be described with reference to FIGS. 1-5.

The present invention relates to a method for determining right ventricle stroke volume comprising the steps of:
provide a plurality of three-dimensional images of right cardiac ventricle of a patient over a cardiac cycle;
identically slicing each of the plurality of images;
selecting an image from the plurality of images, for each time unit of the cardiac cycle;
determining a region of interest in each slice of the selected images, wherein the region of interest shows the right ventricle of the patient;
determining area of the region of interest;
determining volume of the region of interest;
determining total volume of the region of interest for each time unit, wherein the maximum total volume is end diastolic volume and the minimum total volume is end systolic volume; and
determining the right ventricle stroke volume using an equation:

Right Ventricle Stroke Volume=end diastolic volume−end systolic volume (3)

The method of the present invention is illustrated in FIG. 1.

In a preferred embodiment, the three-dimensional are full volume real-time echocardiogram.

Through the cardiac cycle, the heart cavity changes and each change is captured in a frame by the machine. Frame rate refers to how many times in a second, an image is updated. In each frame, there could be consecutive images produced by the echocardiography. The frame rate is not a constant for a machine. The term "time unit" as used herein refers to frame per motion for each change of the shape of the right ventricle cavity. The time unit is not representing any measuring unit but shows each change of the right ventricle cavity.

In a preferred embodiment, the step of identically slicing each of the plurality of images comprises the steps of:
selecting a primary image from the plurality of images;
slicing said primary image to produce a plurality of slices; and
imprinting the plurality of slices on subsequent images of said plurality of images;
thereby identically slicing each of the plurality of images.

In a preferred embodiment, the plurality of images may be sliced into 4, 9, and 16 slices. It is preferred that the plurality of images is sliced into 16 slices. The primary image is selected to be sliced first to provide a standard impression on the plurality of images of the right cardiac ventricle of the patient produced by the machine.

In a preferred embodiment, the region of interest is determined using region growing method and spline tools. Region growing is a simple-based image segmentation method. Region growing method involves selection of initial seed points. The approach to segmentation examines neighbouring pixels of initial seed points and determines whether the pixel neighbours should be added to the region. Seed point is the initial point for a set of region growing. Seed point can be a pixel or a group of pixels which are able to reflect character of an object in image. The selection of seed points may be chosen by using the mean of grey scale value of four neighbouring pixels which can be obtained when calculation of volume of each slice is obtained. After the seed points are selected, spline tools are used to connect the seed points together to form an area. Spline tools are used to enable user to easily create smooth, curved, and precision shapes of the region of interest.

In a preferred embodiment, the area of the region of interest for each slice is determined using an equation:

Area=(Σnumber of pixels in region of interest)×resolution (1)

In a preferred embodiment, the volume of the region of interest for each slice is determined using an equation:

Volume=area×slice thickness (2)

wherein the slice thickness is the distance between each slice in the image.

Below is an example of the method for measuring right ventricle stroke volume from which the advantages of the present invention may be more readily understood. It is to be understood that the following example is for illustrative purpose only and should not be construed to limit the present invention in any way.

EXAMPLE

Below is an example of the method for measuring right ventricle stroke volume.

In the following example, the input is an image of the right cardiac ventricle of a patient provided by an ultrasound machine. As the parameters given by the ultrasound machine may be inadequate to calculate image resolution, resolution of 3-dimensional transducer of the ultrasound machine is first determined. In a preferred embodiment, the resolution of the input is predetermined using an equation:

$$\text{resolution} = \frac{\sum_{i=1}^{p} \text{scale}\left(\frac{\text{real size}}{\text{no. of pixels in image}}\right)_i}{n} \quad (4)$$

wherein p is iteration number and n is number of iteration.
Determining Resolution of Input A test object, for example a piece of meat, is used to determine the resolution of the transducer. The real size of the object is measured. A first ultrasound image is produced using the ultrasound machine.

The number of pixels in the first image of the object is counted. The object is then moved to change the distance between the object and the transducer, and a second image of the object is created.

The change in number of pixels depending on the change of distance between the object and the transducer is recorded. Resolution is then calculated using equation (4). Then the average of resolution in all iterations is calculated. The example data is shown in table 1 below.

TABLE 1

Example data for measuring resolution of the transducer.

| Iteration (p) | Probe Distance (cm) | no. of pixels in image | Real size of object (cm) | Resolution = cm/pixel |
|---|---|---|---|---|
| 1. | 1 | 94.51 | 1 | 0.010581 |
| 2. | 1 | 118.01 | 1 | 0.008474 |
| 3. | 1 | 124.1 | 1 | 0.008058 |
| 4. | 1 | 60.01 | 1 | 0.016664 |
| 5. | 1 | 135.77 | 1 | 0.007365 |

TABLE 1-continued

Example data for measuring resolution of the transducer.

| Iteration (p) | Probe Distance (cm) | no. of pixels in image | Real size of object (cm) | Resolution = cm/pixel |
|---|---|---|---|---|
| 6. | 1 | 131.15 | 1 | 0.007625 |
| 7. | 1 | 135.02 | 1 | 0.007406 |
| 8. | 1 | 60.8 | 1 | 0.016447 |
| 9. | 1 | 207.51 | 2.5 | 0.012048 |
| 10. | 1 | 135.01 | 1 | 0.007407 |
| 11. | 1 | 139.86 | 1 | 0.00715 |
| 12. | 1 | 107.25 | 2.5 | 0.02331 |
| 13. | 2 | 96.01 | 1 | 0.010416 |
| 14. | 2 | 142.25 | 1 | 0.00703 |
| 15. | 2 | 208.5 | 2.5 | 0.01199 |
| 16. | 4 | 78.92 | 1 | 0.012671 |
| 17. | 4 | 51.85 | 1 | 0.019286 |
| 18. | 4 | 113.64 | 2.5 | 0.021999 |
| n = 18 | | | Total Scale Resolution | 0.215927 |
| | | | Resolution | 0.011996 inch/pixel |
| | | | Resolution in cm | 0.0304697 cm/pixel |

In a preferred embodiment, the resolution in inches/pixel is multiplied with a constant 2.54 to obtain resolution in centimeters/pixel.

The resolution obtained from the above calculation is 0.0304697 cm/pixel.

Determining Region of Interest

After pre-determining the resolution, input comprising the plurality of three-dimensional images of the right cardiac ventricle of the patient over a cardiac cycle is received from the echocardiography machine.

The frame rate is not a constant for a machine and this applies to the echocardiography used in this example. In this example, the patient has 73 images during one cardiac cycle. Frame per motion for each change of the shape of the heart cavity is denoted as time unit ($t_1$-$t_{15}$) in table 2.

Figure 2:
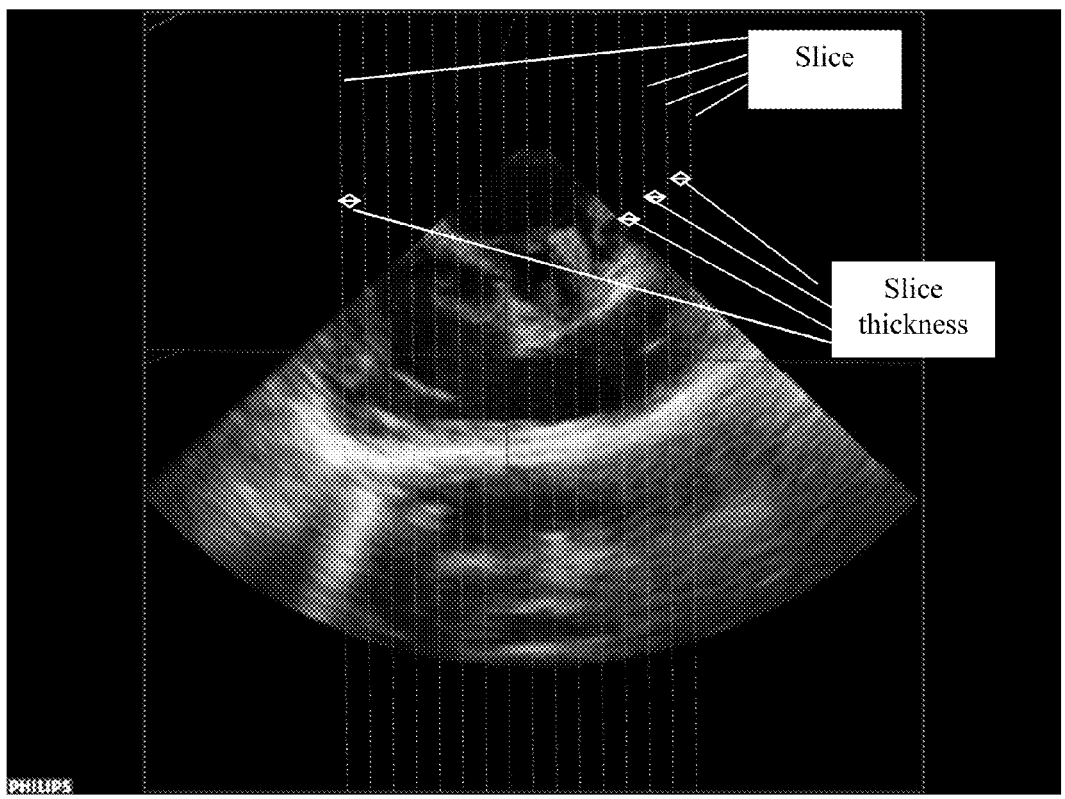
FIG. 2 is a coronal plane ultrasound image, of an input of a full volume image of right ventricle at $t_1$, showing a plurality of slices.

Each of the plurality of images is identically sliced. One of the ways to perform identical slicing to each of the plurality of images is by selecting a primary image from the plurality of images. An example of the primary image is shown in FIG. 2 which is taken at time unit $t_1$. Then, the primary image is sliced into a plurality of slices. As shown in FIG. 2 (a coronal plane ultrasound image sliced in the parallel sagittal plane), there are 16 slices. Then, the plurality of slices is imprinted on subsequent images of said plurality of images so that all of the plurality of images is identically sliced.

An image from the plurality of image is selected for each time unit of the cardiac cycle. For example, in this patient, first time unit, $t_1$, takes one image; second time unit, $t_2$, takes 4 images; third time unit, $t_3$, takes 5 images; fourth time unit, $t_4$, takes 4 images and so on. In further explanation, for example, the third time unit, $t_3$, takes 5 images to show a change of the shape of the right ventricle cavity after the change in $t_2$. The change could be significant in only one of the 5 images or the 5 images could show the gradual change of the right ventricle cavity in $t_3$. When the former occurs, the one image showing the change of the right ventricle cavity is selected; if the latter occurs, the image showing most significant change among the 5 images of the right ventricle cavity is selected. The significant change herein can be the image that shows most apparent change compared to the selected image of the right ventricle cavity in previous time unit.

For each of the selected images, the region of interest for each of the plurality of slices of the selected images is determined, wherein the region of interest shows the right ventricle of the patient. The region of interest in each slice is determined using region growing method.

Method of Selecting a Seed Point in Region Growing Method.

The seed point is the initial point for set of region growing. It can be a pixel or group of pixels able to reflect the region of interest in the ultrasound image of right cardiac ventricle. The minimum pixel intensity in the image is needed for automatic detection of the threshold. The region with the minimum pixel intensity is selected for threshold according to the value of the pixels. The image will then be converted to black and white image by the machine. Each area of the region with the minimum pixel intensity in the image is recorded and a centre of gravity of the area of the region is chosen. Due to the in-homogeneity of the ultrasound image of the pixel intensity in the region of interest, mean value of seed point neighbouring values are used.

Figure 3:
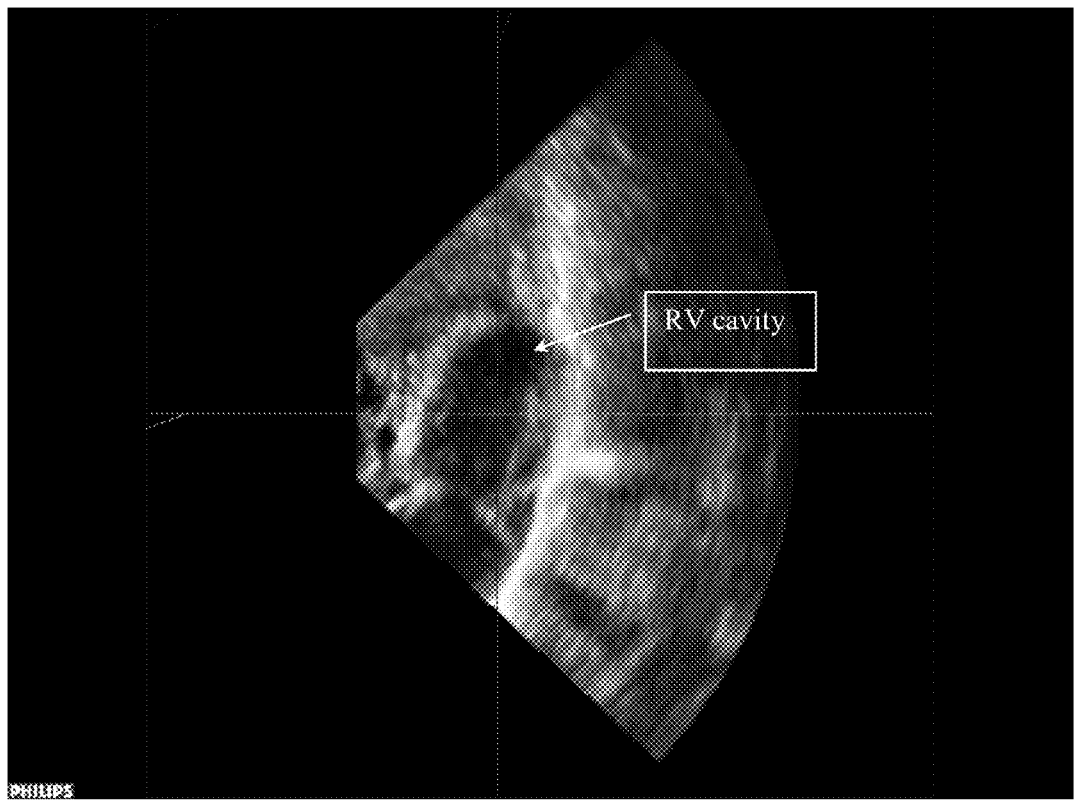
FIG. 3 is a parallel sagittal plane slice of an ultrasound image at $t_1$.
Figure 4:
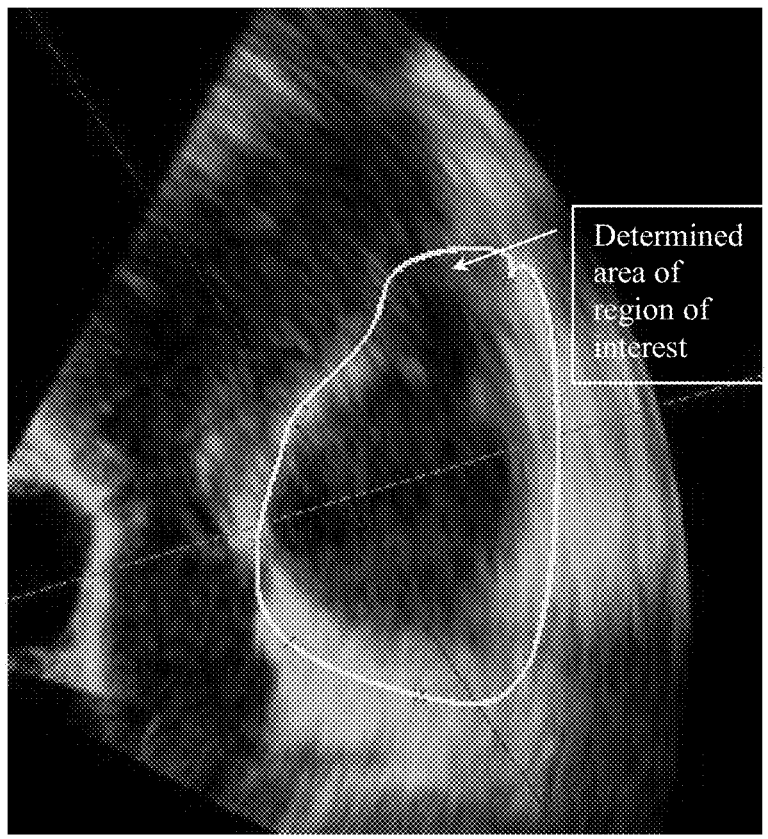
FIG. 4 is a parallel sagittal plane slice of an ultrasound image at $t_1$ showing determination of region of interest in the slice.

FIG. 3 shows an ultrasound image of a slice (parallel sagittal plane) at $t_1$. The desired region of interest in FIG. 3 is right ventricle cavity, denoted as "RV cavity" in FIG. 3 and (B) in FIG. 5. Then, by using region growing method and spline tools, the region of interest is determined as shown in FIG. 4 and (A) in FIG. 5.

Figure 5:
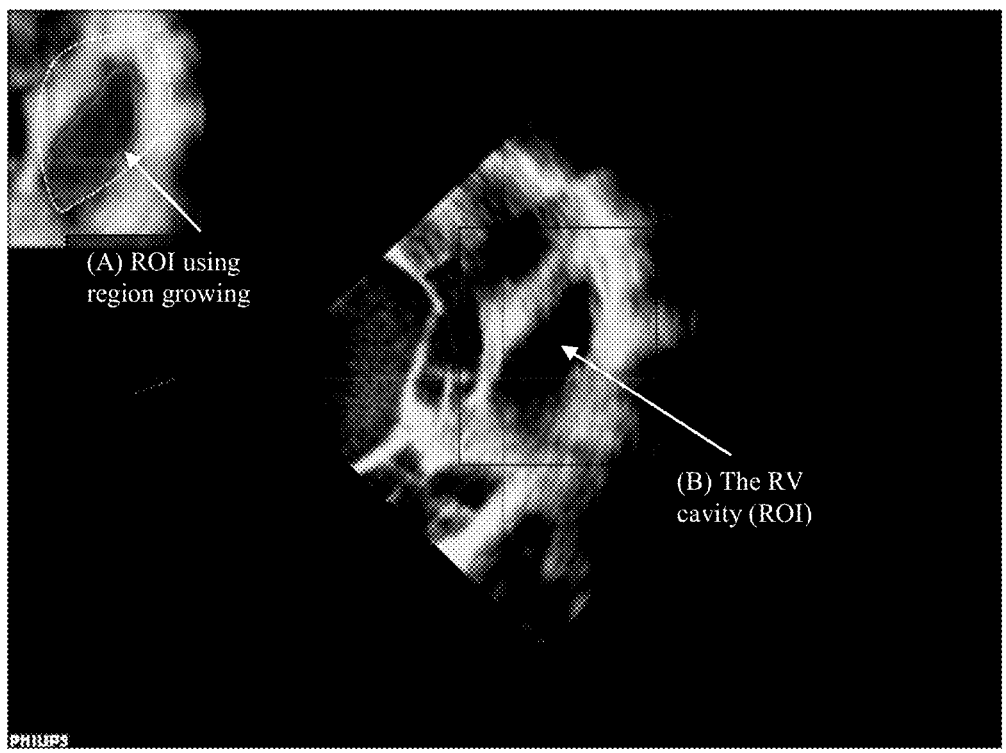
FIG. 5 is parallel sagittal plane slice of an ultrasound image at $t_1$, showing (A) region of interest, shown herein as bolded region; (B) a right ventricle cavity which is the region of interest.

If the ultrasound image is noisy and unclear, Gaussian filter application may be applied to the image to smoothen the image and eliminate any line existing in the ultrasound image. FIG. 5 shows the area of the region of interest after being applied with Gaussian filter.

Calculating Volume of the Region of Interest

Referring to FIG. 5, the area of the region of interest (A) is calculated.

The area of the region of interest is calculated by using equation (1):

$$\text{Area} = (\Sigma \text{number of pixels in region of interest}) \times \text{resolution} \tag{1}$$

Then, the volume of the area of the region of interest is determined.

$$\text{Volume} = \text{area} \times \text{slice thickness} \tag{2}$$

The area is as calculated by using equation (1) previously. The slice thickness is measured as the distance between two slices (referring to FIG. 2).

Referring to FIG. 2, if the distance between each cut is 15 pixels and a resolution of 0.0304697 is as previously calculated, therefore the slice thickness is:

$$\text{Slice thickness} = 15 \text{ pixels} \times 0.0304697 \text{ cm/pixel}$$
$$= 0.45704 \text{ cm}$$

Example data of the volume is shown in table 2.

The total volume of the region of interest for each time unit is then determined wherein the maximum total volume is the end diastolic volume and the minimum total volume is the end systolic volume. Example of this data is also shown in table 2.

The total volume of the region of interest for the plurality of slices 1-16 in the selected image for $t_1$ (referring to table 2) is calculated as:

Total volume for slice 1-16 in $t_1$ =

Slice 1 + Slice 2 + Slice 3 + ... + Slice 16 =

3.812692 + 3.700325 + 3.366682 + 3.523131 +

3.409036 + 3.8598 + 4.356374 + 5.809364 + 7.392439 +

5.642974 + 8.563215 + 9.515739 + 11.12777 +

5.572529 + 4.205976 + 4.425955 = 88.285 ml$^3$.   (5)

This calculation is performed for each of the time units $t_1$-$t_{15}$ of the cardiac cycle.

Calculating Right Ventricle Stroke Volume

Then, the right ventricle stroke volume is determined using equation (3):

Right Ventricle Stroke Volume = end diastolic volume − end systolic volume   (3)

In table 1 of this example, the end of systole is at $t_8$ as $t_8$ shows the lowest total volume (end systolic volume) over the cardiac cycle and the end of diastole is at $t_{15}$ as $t_{15}$ shows the highest total volume (end diastolic volume) over the cardiac cycle. Both values of $t_{15}$ and $t_8$ are applied to equation (3):

$$\text{Right ventricle stroke volume} = \text{End Diastolic Volume (at } t_{15}) - \text{End Systolic Volume (at } t_8)$$

$$= 89.68297 - 28.46554$$

$$= 61.21743 \text{ ml}$$

The end systolic volume is the minimum total volume over all the time units in the cardiac cycle and end diastolic volume is the maximum total volume over all the time units in the cardiac cycle, as shown in table 2.

Although the present invention has been described with reference to specific embodiments, also shown in the appended figures, it will be apparent for those skilled in the art that many variations and modifications can be done within the scope of the invention as described in the specification and defined in the following claims.

TABLE 2

Volume of area of region of interest for each time unit in cardiac cycle

| Slice | $t_1$ | $t_2$ | $t_3$ | $t_4$ | $t_5$ | $t_6$ | $t_7$ | $t_8$ |
|---|---|---|---|---|---|---|---|---|
| Slice1 | 3.812692 | 3.34248 | 3.214987 | 3.024396 | 2.7478 | 2.893013 | 2.846337 | 2.653153 |
| Slice2 | 3.700325 | 3.466516 | 2.619443 | 2.941849 | 2.878751 | 2.629383 | 2.602588 | 2.582708 |
| Slice3 | 3.366682 | 3.44361 | 3.306609 | 3.079283 | 2.801391 | 2.683406 | 2.504051 | 2.39687 |
| Slice4 | 3.523131 | 3.51881 | 3.004515 | 2.714523 | 2.482442 | 2.250793 | 2.034703 | 1.918447 |
| Slice5 | 3.409036 | 3.463058 | 3.432374 | 3.068478 | 2.633273 | 2.264623 | 2.017848 | 1.80003 |
| Slice6 | 3.8598 | 3.648464 | 3.124661 | 2.956976 | 2.928884 | 2.710633 | 2.634569 | 2.229184 |
| Slice7 | 4.356374 | 4.525789 | 4.288522 | 3.30877 | 2.991982 | 2.578386 | 2.475959 | 2.020009 |
| Slice8 | 5.809364 | 5.861657 | 5.356871 | 4.765649 | 4.341248 | 4.274692 | 3.791515 | 3.762559 |
| Slice9 | 7.392439 | 7.398922 | 7.118437 | 6.400586 | 5.896664 | 4.694771 | 4.156275 | 3.947532 |
| Slice10 | 5.642974 | 5.976185 | 7.689779 | 7.304274 | 7.35095 | 7.685457 | 7.879938 | 7.426149 |
| Slice11 | 8.563215 | 8.830734 | 8.598221 | 7.648722 | 7.008231 | 6.824987 | 6.493937 | 6.771396 |
| Slice12 | 9.515739 | 9.62681 | 9.553771 | 8.965142 | 8.579637 | 7.583895 | 7.183264 | 8.084791 |
| Slice13 | 11.12777 | 10.90001 | 10.95274 | 10.46394 | 9.402076 | 8.175117 | 7.497026 | 8.203209 |
| Slice14 | 5.572529 | 5.52715 | 5.600621 | 5.28729 | 4.90654 | 4.457505 | 4.037858 | 3.901289 |
| Slice15 | 4.205976 | 3.938456 | 3.527021 | 3.260798 | 3.314388 | 3.318278 | 3.076257 | 3.067614 |
| Slice16 | 4.425955 | 4.461394 | 4.541347 | 4.756573 | 4.524492 | 4.316182 | 4.08583 | 3.742247 |
| Total Vol. | 88.284 | 87.93005 | 85.92992 | 79.94725 | 74.78875 | 69.34112 | 65.31796 | 28.46554 |

| Slice | $t_9$ | $t_{10}$ | $t_{11}$ | $t_{12}$ | $t_{13}$ | $t_{14}$ | $t_{15}$ |
|---|---|---|---|---|---|---|---|
| Slice1 | 2.724031 | 3.369275 | 3.711994 | 4.133802 | 3.864121 | 3.68347 | 3.853317 |
| Slice2 | 1.694146 | 6.985758 | 3.508005 | 2.695074 | 3.169176 | 3.361928 | 3.405578 |
| Slice3 | 2.306112 | 1.779717 | 1.999697 | 2.384337 | 2.826457 | 3.159236 | 3.219741 |
| Slice4 | 1.769345 | 1.629319 | 1.90721 | 2.614257 | 3.11645 | 3.436695 | 3.581476 |
| Slice5 | 1.951725 | 1.902024 | 2.060634 | 2.469477 | 3.063292 | 3.323464 | 3.503683 |
| Slice6 | 2.773731 | 2.577089 | 2.301791 | 2.829915 | 3.417247 | 3.847266 | 3.954447 |
| Slice7 | 2.039025 | 3.486396 | 2.64062 | 3.911229 | 4.365018 | 4.755277 | 4.704279 |
| Slice8 | 3.729713 | 3.556409 | 4.458369 | 4.76392 | 5.113554 | 5.688353 | 5.649889 |
| Slice9 | 5.960194 | 6.152514 | 5.547462 | 6.194004 | 6.7325 | 7.028976 | 6.955073 |
| Slice10 | 7.050152 | 7.12103 | 6.664648 | 6.552281 | 6.709595 | 6.951183 | 7.181967 |
| Slice11 | 6.752813 | 6.748059 | 6.713916 | 6.93476 | 7.183696 | 7.675949 | 7.713116 |
| Slice12 | 8.997555 | 9.259457 | 8.895993 | 8.87957 | 9.382196 | 9.979901 | 9.878338 |
| Slice13 | 7.98539 | 8.427078 | 8.157398 | 9.110354 | 10.07973 | 10.57717 | 10.49722 |
| Slice14 | 3.675691 | 3.603517 | 4.379712 | 5.299823 | 5.86814 | 6.032368 | 6.073426 |
| Slice15 | 3.069775 | 3.850292 | 3.979513 | 3.844673 | 3.997665 | 4.525789 | 4.602285 |
| Slice16 | 3.868443 | 3.772499 | 4.399592 | 4.874126 | 5.155043 | 5.116579 | 4.909133 |
| Total Vol. | 66.34784 | 74.22043 | 71.32655 | 77.4916 | 84.04388 | 89.1436 | 89.68297 |

We claim:

1. A method for determining right ventricle stroke volume comprising the steps of:
  providing a plurality of three-dimensional images of right cardiac ventricle of a patient over a cardiac cycle;
  identically slicing each of the plurality of images;
  selecting an image from the plurality of images, for each time unit of the cardiac cycle;
  determining a region of interest in each slice of the selected images, wherein the region of interest shows the right ventricle of the patient;
  determining area of the region of interest using Equation 1:

$$\text{Area} = (\Sigma \text{number of pixels in region of interest}) \times \text{resolution} \quad \text{(Equation 1)};$$

determining volume of the region of interest using Equation 2:

$$\text{Volume} = \text{area} \times \text{slice thickness} \quad \text{(Equation 2)},$$

where the slice thickness is the distance between each slice in the image;
  determining total volume of the region of interest for each time unit, wherein the maximum total volume is selected as an end diastolic volume and the minimum total volume is selected as an end systolic volume; and
  determining the right ventricle stroke volume using Equation 3:

$$\text{Right Ventricle Stroke Volume} = \text{end diastolic volume} - \text{end systolic volume} \quad \text{(Equation 3)}, \text{ and}$$

wherein the resolution is calculated casino Equation 4:

$$\text{resolution} = \frac{\sum_{i=1}^{p} \text{scale}\left(\frac{\text{real size}}{\text{no. of pixels in image}}\right)_i}{n},$$

$$\text{(Equation 4)}$$

wherein p is an iteration number, n is the total number of iterations, no. pixels in image is a number of pixels in an object image of a known object, and real size is a measured size of the known object.

2. The method for determining right ventricle stroke volume, according to claim 1, wherein the three-dimensional images are full volume real-time echocardiogram images.

3. The method for determining right ventricle stroke volume, according to claim 1, wherein the step of identically slicing each of the plurality of images comprises the steps of:
  selecting a primary image from the plurality of images;
  slicing said primary image to produce a plurality of slices; and
  imprinting the plurality of slices on subsequent images of said plurality of images, thereby identically slicing each of the plurality of images.

4. The method for determining right ventricle stroke volume, according to claim 1, wherein the region of interest is determined using region growing method and spline tools.

* * * * *